United States Patent [19]
Avnir et al.

[11] Patent Number: 5,371,018
[45] Date of Patent: * Dec. 6, 1994

[54] QUALITATIVE AND QUANTITATIVE PROCESSES FOR REACTIVE CHEMICALS IN LIQUIDS USING DOPED SOL-GEL GLASSES

[75] Inventors: David Avnir; Michael Ottolenghi; Ovadia Lev, all of Jerusalem, Israel

[73] Assignee: Yissum, Research Development Company of the Hebrew University of Jerusalem, Jerusalem, Israel

[*] Notice: The portion of the term of this patent subsequent to Mar. 8, 2011 has been disclaimed.

[21] Appl. No.: 953,358

[22] Filed: Sep. 30, 1992

Related U.S. Application Data

[60] Division of Ser. No. 774,104, Oct. 11, 1991, Pat. No. 5,308,495, which is a continuation-in-part of Ser. No. 738,039, Jul. 31, 1991, abandoned, which is a continuation-in-part of Ser. No. 637,873, Jan. 8, 1991, Pat. No. 5,300,564.

[30] Foreign Application Priority Data

Jan. 23, 1990 [IL] Israel ......................... 93134

[51] Int. Cl.$^5$ ............................. G01N 33/20
[52] U.S. Cl. .......................... 436/73; 436/84; 436/163; 436/164; 436/165; 436/169; 422/59
[58] Field of Search ............. 436/73, 84, 163, 164, 436/165, 169; 422/59, 61, 55–57, 68.1; 525/54.1; 514/2, 21; 530/402, 403, 405, 409, 811; 501/12, 32

[56] References Cited

U.S. PATENT DOCUMENTS

| | | | |
|---|---|---|---|
| 3,896,092 | 7/1975 | Epton et al. | 210/198.2 |
| 3,930,951 | 1/1976 | Messing . | |
| 4,148,689 | 4/1979 | Hino et al. . | |
| 4,335,017 | 6/1982 | Miles et al. | 210/656 |
| 4,436,823 | 3/1984 | Blumcke et al. | 436/73 |
| 4,851,373 | 7/1989 | Hench et al. . | |
| 4,880,851 | 11/1989 | Yamamoto . | |
| 4,941,993 | 7/1990 | Strehlow et al. . | |
| 5,009,688 | 4/1991 | Nakanishi . | |
| 5,076,980 | 12/1991 | Nogues et al. . | |

OTHER PUBLICATIONS

B. Fried and J. Shema, Thin Layer Chromatography Techniques and Applications, Chromatographic Science Series, vol. 17, Marcel Dekker, New York (1982) p. 231.

E. Jungris, Spot Test Analysis, Wiley, New York, (1985).

The Merck Index pp. 38,952,1037 (1983).

Song-Ping Liang et al, "Covalent Immobilization of Proteins and Peptides for Solid–Phase Sequencing Using Prepacked Capillary Columns", Analytical Biochemistry 188, (1990), pp. 366–373.

Vered R. Kaufman et al, "Water Consumption During the Early States of the Sol–Gel Tetramethylorthosilicate Polymerization as probed by Excited State Proton (List continued on next page.)

*Primary Examiner*—James C. Housel
*Assistant Examiner*—Jan M. Ludlow
*Attorney, Agent, or Firm*—Lowe, Price, LeBlanc & Becker

[57] ABSTRACT

A process for qualitative or quantitative determination of a reactive chemical contained in a liquid sample by forming doped sol-gel glass pellets from a metal alkoxide, arranging the porous doped sol-gel glass pellets in a glass tube, contacting a liquid sample containing a reactive chemical with the porous doped sol-gel glass pellets contained in the glass tube, and measuring a length of a stained portion of the glass tube resulting from a color change in the sol-gel glass pellets. The sol-gel glass pellets are formed by a gelling step conducted at room temperature in the presence of a colorimetric reagent dopant which produces a color change in the presence of the reactive chemical, and a drying step conducted at not greater than 41° C. The doped sol-gel glass pellets contain the colorimetric reagent dopant encapsulated therein and the encapsulated colorimetric reagent dopant is color changeable in the presence of the reactive chemical in the pores of the doped sol-gel glass pellets.

10 Claims, 5 Drawing Sheets

OTHER PUBLICATIONS

Transfer", Journal of Non-Crystalline Solids 99 (1988), pp. 379–386.

Vered R. Kaufman et al, "Structural Changes Along the Sol–Gel–Xerogel Transition in Silica As Probed by Pyrene Excited-State Emission", Langmuir 1986, 2, pp. 717–722.

David Avnir et al, "The Nature of the Silica Cage as Reflected by Spectral Changes and Enhanced Photostability of Trapped Rhodamine 6G", J. Phys, Chem. 1984, 88, pp. 5956–5959.

Ichiro Chibata et al, "Production of L–Aspartic Acid by Microbial Cells Entrapped in Polyacrylamide Gels", Methods of Enzymology 44(XLIV) (1976), pp. 739–746.

Professor J. F. Kennedy, "Data on Techniques of Enzyme Immobilization and Bioaffinity Procedures", Chapter 4, pp. 380–420.

Professor J. F. Kennedy, "Principles of Immobilization of Enzymes", Chapter 4, pp. 147–207.

R. E. Majors, J. of Chromatographic Science, 15, 334 (1977).

E. Stahl, Thin Layer Chromatography, 2nd Ed., SpringerVerlag, Berlin (1969) p. 48.

Brinker, C. J., Scherer, G. W., Sol–Gel Science, Academic Press, San Diego (1990).

P. Roper, Am. Ind. Hygiene Assoc. J. 35, 438 (1974).

APHA, AWWA, WPCF, Standard Methods For the Examination of Waster and Wastewater, APHA, Washington, D.C., 17th Ed. (1989) pp. 2–30.

Caturan et al, "Inorganic Gels for Immobilization of Biocatalysts", J. of Mole. Catalysts, 57 (1989) L13–L16.

QUALITATIVE AND QUANTITATIVE PROCESSES FOR REACTIVE CHEMICALS IN LIQUIDS USING DOPED SOL-GEL GLASSES

RELATED APPLICATIONS

This application is a division of application Ser. No. 07/774,104 filed Oct. 11, 1991, now U.S. Pat. No. 5,308,495 which is a continuation-in-part of application Ser. No. 07/738,039, now abandoned filed Jul. 31, 1991, which is a continuation-in-part of U.S. Ser. No. 07/637,873, filed Jan. 8, 1991 now U.S. Pat. No. 5,300,564.

BACKGROUND OF THE INVENTION

The efficiency of all chromatographic methods (i.e. column or planar and gas or liquid chromatographies) is largely dependent on the properties of the chromatographic media. Therefore, extensive research efforts have been devoted to the invention of a plethora of chromatographic packings tailored for a variety of specific separation needs. Silica based packings are particularly suitable for chromatographic applications since they are thermally stable, chemically inert, can be manufactured in various geometrical configurations and their pore size and bulk density can be predetermined. Moreover, the polarity of silica based matrices can be modified by covalent bonding of organic compounds onto the polar glass matrix (R. E. Majors, J. of Chromatographic Science, 15, 334 (1977)) or by impregnation of the silica gel glass with organic compounds (E. Stahl, Thin Layer Chromatography, 2nd ed., Springer-Verlag, Berlin (1969) p. 48).

The recent new innovation of doped sol-gel glasses (described in the U.S. Pat. application Ser. No. 07/637,873) provides a new class of ceramic packings for chromatography that incorporates characteristics of silica glasses as well as other advantages:

1. The characteristics of the sol-gel glasses, including glass configuration, pore size, density and glass polarity can be tailored to any required need. These can be achieved, for example, by changes of the ratio between the alkoxysilane/water/alcohol in the polymerization solution, or by incorporation of trialkoxysilane compounds in the polymerization solution (Brinker, C. J., Scherer, G. W., Sol-Gel Science, Academic Press, San Diego (1990)).

2. The exact chemical characteristics of the solid support including their interaction with the target chromatographic compounds can be controlled by suitable chemical dopants. A wide range of compounds including ion exchange compounds (such as those containing carboxylic, sulfonic, aminic and ammonium groups) have been successful entrapped in solid sol-gel glasses in a relatively simple procedure.

3. The doped sol-gel glasses maintain the transparency of the sol-gel glasses except for the absorbance window of the dopants. This property is particularly important for such chromatographic methods where visualization and quantitation of the separated compounds are manifested when the compounds are still in the chromatographic media (e.g. Thin Layer Chromatography and spot tests which are discussed below).

4. The doped sol-gel glasses are highly porous even when chemical dopants are incorporated into the polymerization step.

5. The chemical modification of the sol-gel glass by the doping process is more stable than impregnated layers and more simply performed than covalent bonding of organic coatings.

In the following we shall present typical chromatographic and spot test applications demonstrating the possibility to use doped sol-gel glasses for planar or column chromatographic applications in gas or liquid analysis. The chromatographic applications and the ion exchange properties of doped sol-gel glasses were disclosed in the U.S. patent application No. 07/637,873 without experimental demonstration. Analytical spot testing and length of stain detectors were disclosed but were not mentioned specifically in the patent application.

BRIEF DESCRIPTION OF THE DRAWING

The present invention will be more readily understood in view of the drawing, in which FIGS. 1a, 1b and 1c disclose selectivity isotherms of glass immobilized Aliquat 336: a. $Br^-/Cl^-$; b. $NO_3^-/Cl^-$; c. $SO_4^-/Cl^-$; ($C_a$, $Y_a$ represent concentrations of the counter ion and $C_{Cl}$, $Y_{Cl}$ represent the concentrations of chloride in the solution and glass phase, respectively).

A. Selective Adsorbents

Figure 1A:
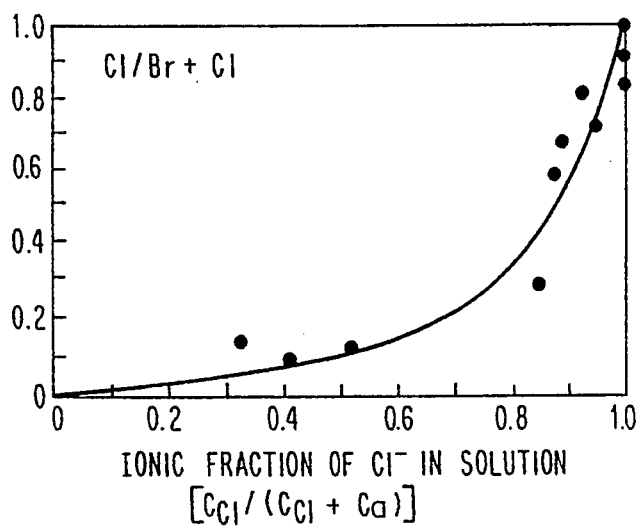

It has been demonstrated in patent application number 07/637873 (e.g., example B therein) that doped sol-gel glasses can be used for selective concentration of specific compounds from the solution into the glass phase. Here we further demonstrate that doped sol-gel glasses may serve as adsorbents for classes of chemical compounds when appropriate chemical dopants are incorporated into the sol-gel glasses. The driving force for this concentrating power can be physicochemical adsorption, complex formation (e.g. concentration of divalent iron by doped phenanthroline), ion pair formation (e.g., concentration of cadmium(II) by forming ion pairs with doped eosin Y and 1,10-o-phenanthroline), ion exchange mechanism etc . . . In example A below we demonstrate the possibility to synthesize anion exchangers by using the sol-gel doping procedure. Specifically, we demonstrate the possibility to produce sol-gel glasses doped with aliquat 336 (technical trioctylmethylammonium chloride) and that such glasses exhibit ion exchange properties and selective uptake of several ions (e.g. sulfate, nitrate and bromide over chlorides).

B. Chromatographic Applications

The selective interaction of doped sol-gel glass with the surrounding chemical compounds makes this type of glasses a promising chromatographic media. This possibility was specifically mentioned in the above mentioned patent application. In examples B-F we demonstrate planar and column chromatographies for liquid and gas applications. Monolithic doped sol-gel glasses can also be used for the same purpose.

This layer chromatographic methods using doped sol-gel glasses are particularly attractive due to the low cost of doped sol-gel glasses. Moreover, by doping appropriate photometric reagents the separation (e.g., by adsorption, complex formation or even by chemical reaction), visualization and quantitation of the various compounds can be done in one step. In example B we demonstrate the usage of doped glasses for Thin Layer Chromatographic separation and spot visualization in one step.

The separation of chemical compounds by liquid chromatography is often hindered by the presence of interfering substances. For example, the separation of amino acids by thin layer chromatography is hindered in the presence of high concentrations of chelating agents and particularly metallic cations (e.g. ferrous ions). A sample cleanup pretreatment to remove the amino acids from the inorganic ions is recommended (B. Fried and J. Sherma, Thin layer chromatography Techniques and applications, Chromatographic science series, volume 17, Marcel Dekker, N.Y. (1982) p 231). Such a clean up procedure may become very complicated when only a small quantity of the sample is available. In example C we demonstrate that incorporation of a few percent of sol-gel glasses doped with appropriate ligands, that chelate the interfering substance (e.g., 1,10-o-phenanthroline to remove ferrous ion interferences), into the TLC plate improve the separation capability of the chromatographic method.

C. Spot testing and Tube Detectors

Spot testing is a diagnostic technique to quantitate or determine chemical compounds by the color and size of stains that are formed when the sample is interacted with a solid substrate (containing appropriate photometric reagents). Spot test diagnostics have found many quantitative and qualitative applications in medical, food, environmental, agricultural and industrial diagnostics (E. Jungris, Spot test analysis, Wiley, New York, N.Y., (1985)). Doped sol-gel glasses are particularly suitable for spot test diagnostics. In the following we shall discuss few areas of applications which combine spot testing with the chromatographic advantages of the doped sol-gel glasses.

C.1. Gas Phase Analysis

Occupational safety and indoor air quality practitioners make extensive usage of Length of Stain Tube Detectors (e.g. P. Roper, Am. Ind. Hygiene Assoc. J. 35, 438 (1974)). When using this type of detector, air is sampled through a vial containing glass pellets impregnated with colorimetric reagents. The analyzate reacts with the reagent to form a colored (stained) section of the vial whose length depends on the concentration of the analyzate in the sampled air. Length of stain detectors exhibit short shelf life due to the low adhesion of impregnated reagents to the supporting glass. Length of stain detectors can be regarded as displacement chromatography. In both cases the isolated compound (or its reaction product) accumulates in a certain section of the chromatographic column and the front of this section propagates downstream when more material accumulates. In example D we demonstrate Length of Stain Detectors using sol-gel glasses doped with a pH indicator for determination of acidity or alkalinity in air. We anticipate that such glasses will have superior shelf life compared with impregnation products.

C.2. Liquid Phase analysis

Length of Stain Detectors are seldom used for the analysis of aqueous solutions since the colorimetric reagents leach out of the glass support when water is introduced. The strong entrapment of reagents in the doped sol-gel glasses makes the production of tube detectors for aqueous analysis possible. In example E we demonstrate tube detectors for quantitative determination of cobalt, iron and aluminum ions in aqueous solution.

Acidity and Alkalinity of water represent its quantitative capacity to react with a strong base and a strong acid (respectively) to a designated pH (APHA, AWWA, WPCF, Standard Methods for the examination of water and wastewater, APHA, Washington DC, 17th ed., 1989 p. 2-30). In the following we discuss Alkalinity but the same principles hold for the entire pH scale and for titration with acid or base.

Since alkalinity is an aggregate property representing an overall sum of all acid consuming species in the water the current recommended methods for its quantitation are based on titrimetric studies by strong acid (APHA, AWWA, WPCF, Standard Methods for the examination of water and wastewater, APHA, Washington DC, 17th ed., 1989 p. 2-35). The alkalinity of a water depends on the end point pH level of the titration. For example, phenol-phthalein alkalinity represents the quantity measured by titration to pH 8.3 and total alkalinity refers to titration to pH 4.3.

In example F we demonstrate that (pH indicator) doped sol-gel tube detectors can serve as alkalinity detectors and that the length of stain produced when water is sampled through the tube detectors represent alkalinity rather than pH measurement. Selection of end point pH level can be manifested by an appropriate choice of the doped pH indicator.

D. Crack prevention

It is well known that sol-gel glasses tend to crack during the wetting or drying periods. We demonstrate that doping the glasses with surface active agents such as quaternary ammonium compounds prevent cracking of the glasses with no significant lose of photometric activity.

EXAMPLES

A. Preparation of doped sol-gel glasses exhibiting anion exchange properties In this section we exemplify the possibility to prepare anion exchangers using doped sol gel glasses, in accordance with the above mentioned U.S. patent application. Sol-gel glasses doped with aliquat 336 (technical trioctylmethylammonium chloride) are shown to exhibit ion exchange properties and selective uptake of several ions over chlorides. Experimental details for the preparation of sol gel glasses: A solution of methanol, water and aliquat 336 was prepared and mixed with tetramethoxysilane (TMOS) in a 20 ml bottle. Typical weight ratios employed were (H$_2$O/methanol/TMOS/organic dopant)=(2.9/3.0/2.2/0.1–0.4). The bottles were covered with aluminum foil and were let to stand for several days. After the gel was formed the glasses were transferred to a 40° C. incubator for two weeks until no weight loss was detected. The glasses were then grinded prior to the selectivity tests.

Selectivity experiments

The glasses containing doped anion exchanger were immersed in a 1N NaCl solution for several hours to remove traces of undersirable anions. The glasses were then washed thoroughly with distilled water and dried in a 50° C. oven. Approximately one gram of the glass was immersed in 100 ml distilled water and allowed to stand for one day, after which stock solutions containing the counter ion (Br$^-$, SO$_4^-$, NO$_3^-$) were added. The glasses were shaked gently on an Arig-Levi shaker for several hours until equilibrium was reached. The concentrations of the anions in the solution were analyzed by ion chromatography.

Results

Figure 1B:
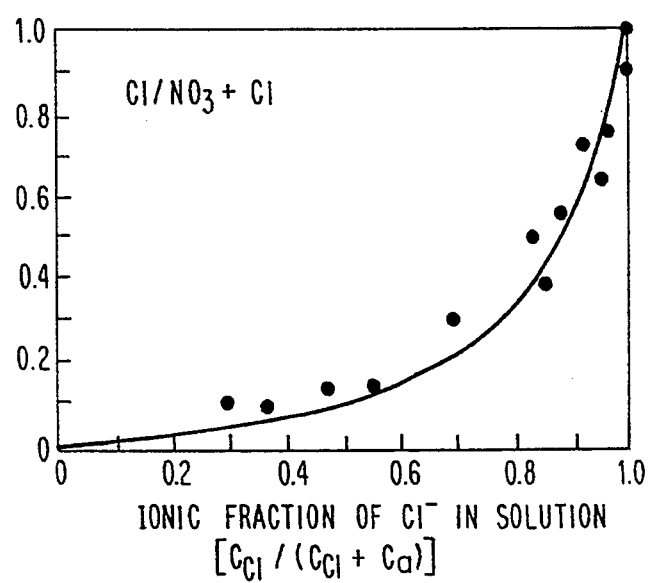
Figure 1C:
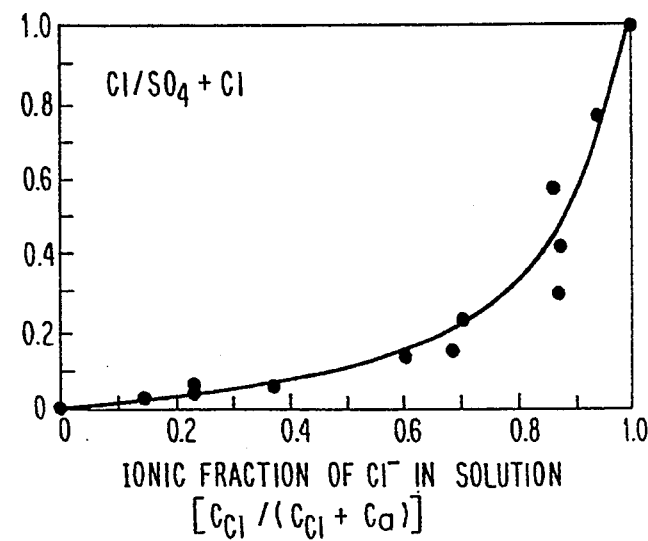

FIGS. 1a–c demonstrate the binary exchange isotherms of SO$_4^-$, Br$^-$ and NO$_3^-$ versus Cl$^-$ in glasses doped with Aliquat 336. Where $C_a$ and $C_b$, $y_a$ and $y_b$ are the equilibrium concentrations of the counter ions a or b in the solution and in the resin phase respectively.

The following test confirmed that the exchange capacity of the doped glasses is due to entrapped ammonium groups rather than adsorption phenomena. Porous glasses prepared by the Sol-Gel process without any addition of organic dopant were immersed in a saturated solution of Aliquat 336. The glasses were then washed with one liter of distilled water according to the same procedure applied to the doped glasses prior to the selectivity tests. Exchange experiments with these glasses did not reveal any detectable exchange capacity, confirming that the immobilization of the ammonium salts in the polymerization process cannot be attributed to an adsorption mechanism only.

B. Thin Layer Chromatographic Detectors for separation and visualization of chemical species In the following we exemplify the usage of doped glasses for Thin Layer Chromatographic separation and spot visualization in one step.

Experimental Details

Glass preparation: Glasses doped with 5% (weight) of 1,10-o-phenanthroline or 5% 1-nitroso-2-naphthol were prepared according to the general method reported in Example B of the U.S. patent application No. 07/637,873. In a typical procedure 2.5 ml tetramethoxysilane (petrarch), 3.0 ml methanol, 2.4 ml distilled water, 0.5 ml of 1 mM NaOH solution and 3.0 ml containing 1,10-o-phenanthroline solution were mixed, allowed to gel and dried to a constant weight at 41° C. for three days. The dried glass contained 5.0% weight o-phenanthroline. An appropriate amount (Tables 1,2) of doped sol-gel glasses were crushed with 3.6 gr. of 70–230 mesh ASTM Kieselgel 60 (Merck) in a chinaware cup and sieved by a sieve shaker. The glass fraction smaller than 0.07 mm was used for the TLC plate preparation.

TLC plates preparation: TLC plates were prepared according to standard procedures (E. Stahl, Thin Layer Chromatography, Springer-Verlag, Berlin, 2nd ed.) in a typical experiment a mixture of 0.2 gr. anhydrous CaSO$_4$, 0.15 gr. Starch (Baker), 2.65 gr. crushed glasses were mixed with 10 ml distilled water. The slurry was spread on microscope slides (26×76 mm) forming 0.05 cm thick coatings.

Iron Detection: TLC plates containing different percent of sol-gel glasses doped with 1,10-o-phenanthroline solution were developed in samples containing various concentrations of ferrous ammonium sulfate.

Cobalt/iron/copper detection: TLC plates of glasses doped with 0.0375% 1-nitroso-2-naphthol were exposed to several solutions containing various concentrations of cobaltous chloride, copper chloride and ferrous ammonium sulfate.

Results: Table 1 presents the lengths of stains developed after exposure of TLC Detection plates to various iron(II) samples as a function of the concentration of 1,10-o-phenanthroline in the chromatographic media. The length of stain was shown to follow (regression coefficient, R=0.983) the empirical equation:

$$L = 112.6 + 22.369 \log([Fe]) - 128.2P$$

where,
L=length of stained section (mm)
[Fe]=iron concentration in the sample (mole/liter)
P=o-phenanthroline weight percent in the TLC plate.

Table 2 depicts the lengths of the stained sections what were produced by exposure of 1-nitroso-2-naphthol plate detectors to different concentrations of copper and cobalt ions. Since the 1-nitroso-2-naphthol complexes with iron and cobalt exhibit different colors it is possible to separate the two compounds by a single TLC plate detector and to quantitate both concentrations with no need for further visualization technique. Thus, combining TLC separation ability, color visualization and quantitation into one step.

In a different experiment copper, cobalt and ferrous ions were separated using the same type of 1-nitroso-2-naphthol TLC plate. However, because the complexes of iron and copper exhibit similar shades of green it was necessary to distinguish between these two sections by further visualization with ammonia vapors.

TABLE 1

CALIBRATION EXPERIMENTS OF IRON(II) TLC PLATE DETECTORS

| % O-Phenanthroline in glass | Length of Stain (mm) | | | | |
|---|---|---|---|---|---|
| | 0.033 | 0.043 | 0.066 | 0.075 | 0.099 |
| IRON Conc. (M) | | | | | |
| 0.00005 | 13.5 | 13.5 | 9.5 | 7.5 | 5.0 |
| 0.0001 | 18.5 | 18.75 | 15.0 | 14.5 | 12.0 |
| 0.00025 | 26.0 | 26.0 | 21.5 | 22.5 | 19.0 |
| 0.0005 | 36.0 | 36.0 | 33.0 | 27.5 | 24.5 |
| 0.001 | 43.75 | 42.5 | 39.0 | 38.0 | 35.0 |

TABLE 2

LENGTHS OF STAINS PRODUCED BY TLC PLATE DETECTORS

| Analyzate: | | | |
|---|---|---|---|
| Co(II) | Cu(II) | Co(II) | Cu(II) |
| CONCENTRATIONS (mM) | | Length of Stains (mm) | |
| 0.375 | 5.0 | 1.0 | 10.0 |
| 0.75 | 5.0 | 2.0 | 9.0 |
| 1.5 | 5.0 | 3.0 | 9.0 |

TABLE 2-continued
LENGTHS OF STAINS PRODUCED BY TLC PLATE DETECTORS

| Analyzate: | | | |
|---|---|---|---|
| Co(II) | Cu(II) | Co(II) | Cu(II) |
| CONCENTRATIONS (mM) | | Length of Stains (mm) | |
| 1.5 | 10.0 | 2.0 | 16.0 |

C. Masking chromatographic interferences by incorporation of doped sol-gel glass into the chromatographic media In the following example we demonstrate that the separation of amino acids containing high concentration of iron(II) can be improved by the addition of a few percent of 1,10-o-phenanthroline doped sol-gel glasses into the thin layer chromatographic media.

Experimental details

Preparation of doped sol-gel glass: Preparation of sol-gel glasses doped with 1,10-o-phenanthroline was conducted according to the general procedure outlined in example B above. In a typical procedure 2.5 ml tetramethoxysilane (Petrarch), 3.0 ml methanol, 2.4 ml distilled water, 0.5 ml of 1 mM NaOH solution and 3.0 ml containing 1,10-o-phenanthroline solution were mixed, allowed to gel and dried to a constant weight at 41° C. for three days. The dried glass contained 1.0% weight o-phenanthroline.

Preparation of TLC plates

The doped sol-gel glasses were crushed in a chinaware cup and sieved by a sieve shaker. The glass fraction smaller than 0.07 mm was used for the TLC plate preparation. 0.5 gr of doped sol gel glass and 3.6 gr. of 70-230 mesh ASTM Kieselgel 60 (Merck) were mixed with 0.6 gr. anhydrous $CaSO_4$, 0.3 gr. starch and 9 ml distilled water. The slurry was spread on 5×20 cm glass plates. The TLC plates were than dried for 2 Hours in a 80° C. oven forming solid 0.5 mm thick coatings.

Control plates, using the same ingredients without doped sol-gel glasses were prepared following the same procedure.

Amino-acid separation: One microliter aqueous solution containing freshly prepared 0.33 mg/ml L-histidine, 0.33 mg/ml D-phenylalanine, 0.33 mM ferrous ammonium sulfate and 0.067 gr/ml n-propanol was applied to each plate. A mixture of 70% ethanol (95% pure) and 30% distilled water was used as eluent. Visualization of the spots was done by spraying 2% (weight) ninhydrin in ethanol solution followed by heating to 110° C.

Results

Figure 2A:
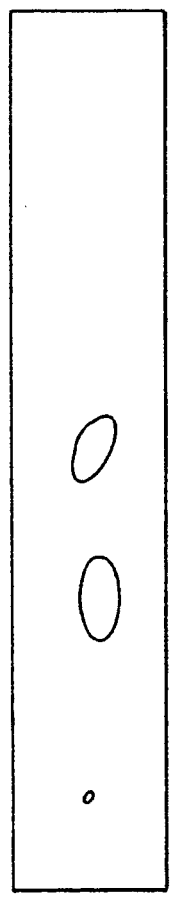
FIGS. 2A and 2B disclose amino acid separation in the presence of ferrous ions: A. separation by a TLC plate that contains doped sol-gel glasses; B. separation by a TLC plate without doped glasses.
Figure 2B:
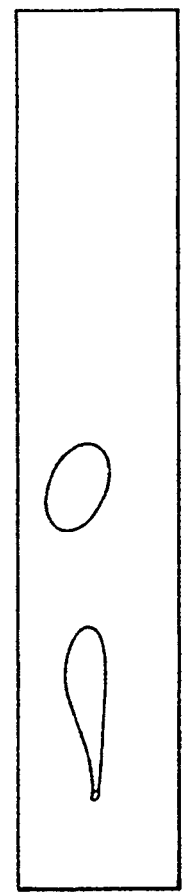

FIG. 2 depicts a comparison of the separation achieved by the two TLC plates. The $R_s$S and the dimensions of the spots of the two amino acids in the TLC plate containing doped sol-gel glasses (plate A) were unaffected by the presence of ferrous ions. The spot size and the $R_s$ of the L-Histidine was considerably distorted in the presence of ferrous ions when the control TLC plate (without doped glass) was used (plate B).

D. Tube Detectors for Gas Analysis

In the following we demonstrate (Length of Stain) Tube Detectors containing methyl-orange doped sol-gel glasses for the determination of acidity and alkalinity in air.

Experimental details

Glass Preparation: Sol-gel glasses doped with 0.05% methyl-orange indicator were prepared according to the procedure in example B.

Preparation of tube detectors: Glass capillaries (0.7 mm in diameter and 10 cm length) were filled (up to 3/4 of their length) with Sol Gel glass pellets doped with the methyl orange reagent. The tubes were stoppered at both ends by 3 mm filter papers to hold the glass pellets in place.

Air Detection: Air was drawn by a vacuum pump through a solution containing either 25% ammonium hydroxide or 36% aqueous solution of hydrochloric acid and then through a methyl orange tube detector which has originally been in its acidic or basic form respectively.

Results

Figure 3A:
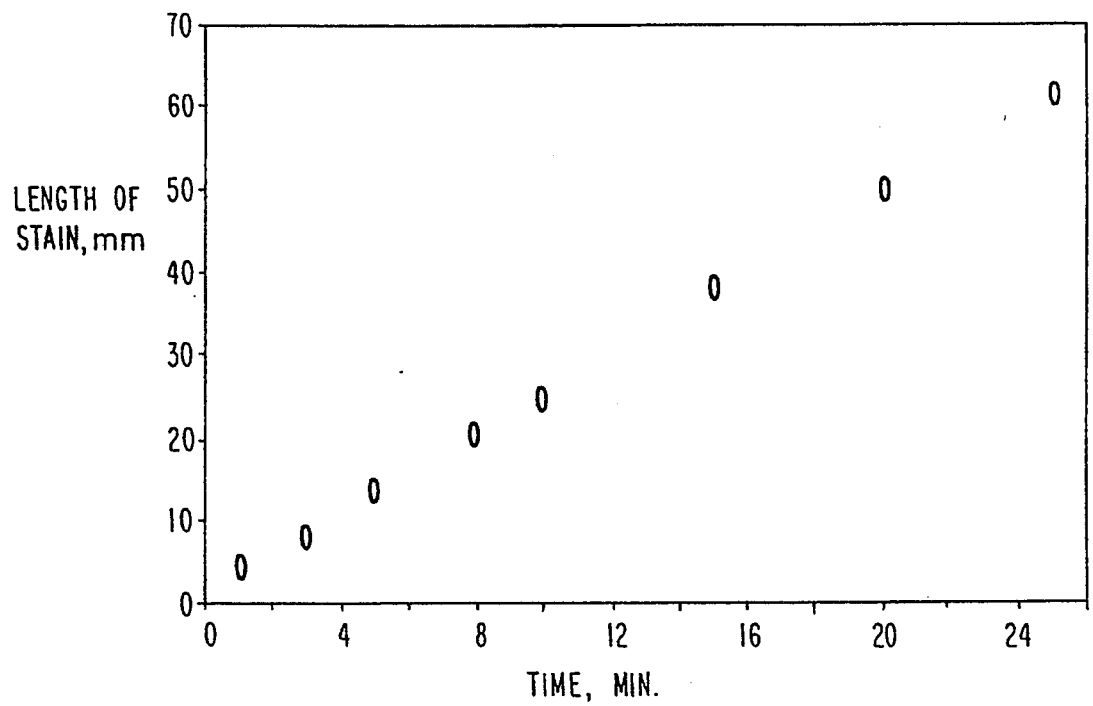
FIGS. 3A and 3B disclose the length of stain development in alkalinity tube detectors: A. transition from acidic form of methyl orange doped glasses to the basic form of the detector; B. transition from basic to acidic form.
Figure 3B:
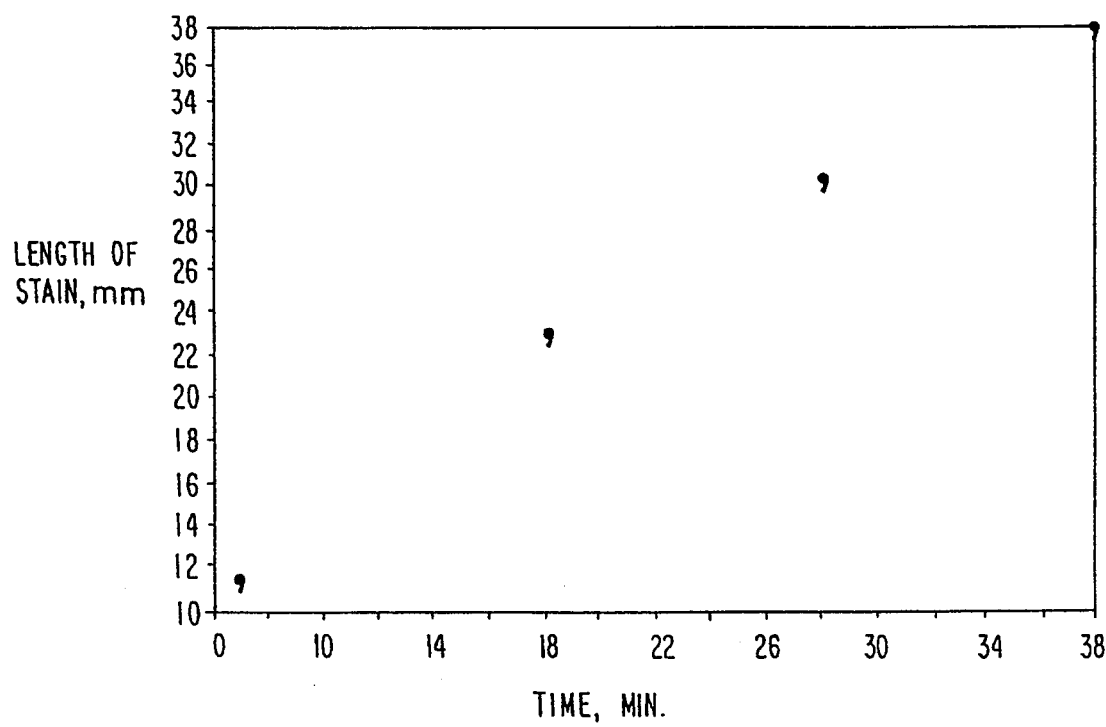

FIG. 3A depicts the color front (from yellow to orange) propagation when 0.03 ml/minute of air containing ammonium hydroxide was passed through pH tube detector. FIG. 3B depicts a color front (from orange to yellow) propagation when 0.03 ml/minute of acidic air was passed through the detector. In both cases the front was very sharp and its position could be accurately detected visually.

E. Tube Detectors for Liquid Phase Analysis

The strong entrapment of reagents in the doped sol-gel glasses makes the production of tube detectors for aqueous analysis possible. In the following we shall demonstrate tube detectors for quantitative determination of cobalt, iron and aluminum ions in aqueous solution.

Experimental details

Glass preparation: The experiments were carried out using Sol-Gel glasses prepared according to standard Sol-Gel procedures depicted above: In a typical procedure 5.0 ml tetramethoxysilane (Petrarch), 6.0 ml methanol solution containing the reagent, 1.2 ml distilled water and a 1 ml 1 mM NaOH solution (added for base catalysis) were mixed, allowed to gel and dried to constant weight at 41° C. for three days. A typical reagent solution (e.g. the solution used for preparation of the iron glass detector in FIG. 4) contained 70 mg 1,10-o-phenanthroline. After drying, the glasses were crushed in a chinaware cup and sieved by a sieve shaker. The fractions between 0.5-0.4, 0.4-0.2, 0.2-0.1 mm and the glass pellets smaller than 0.1 mm were collected for further experiments.

Preparation of tube detectors: Glass capillaries (0.7 mm in diameter and 10 cm length) were filled (up to 3/4 of their length) with Sol Gel glass pellets doped with the colorimetric reagents. The tubes were stoppered at both ends by 3 mm filter papers to hold the glass pellets in place.

Calibration curves: The following method was used in order to determine the response of tube detectors to different concentrations of target analyzates. One end of the tube detector was immersed in approximately 2 mm deep sample solution. Capillarity forces drive the solution upward through the tube detectors. As the solution front advances up, a second color front marking the upper end of the stained portion of the Sol-Gel doped glasses ascends. The length of the stained portion of the glasses can be measured after the solution reaches the upper end of the capillary or after a certain amount of solution is passed through the glass column.

In some experiments the capillarity force was replaced by an external pumping device such as positive displacement pump or hydrostatic pressure.

Results

Figure 4C:
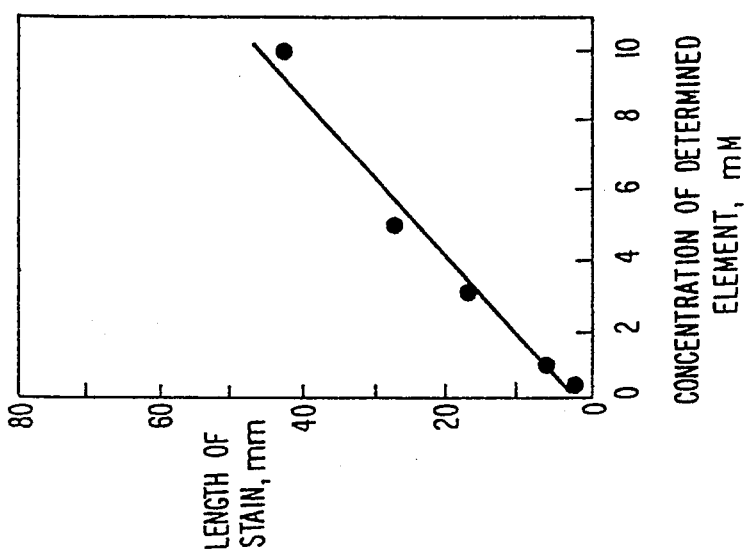
FIGS. 4a, 4b and 4c disclose the response of several tube detectors to different concentrations of elements in water: a. Iron(II) detectors containing 1.7% 1,10-o-phenanthroline, pH=4.0; Cobalt(II) detectors containing 0.03% 1-nitroso-2-naphthol, pH=6.0; c. aluminum detectors containing 0.5% alizarin, pH=4.
Figure 4B:
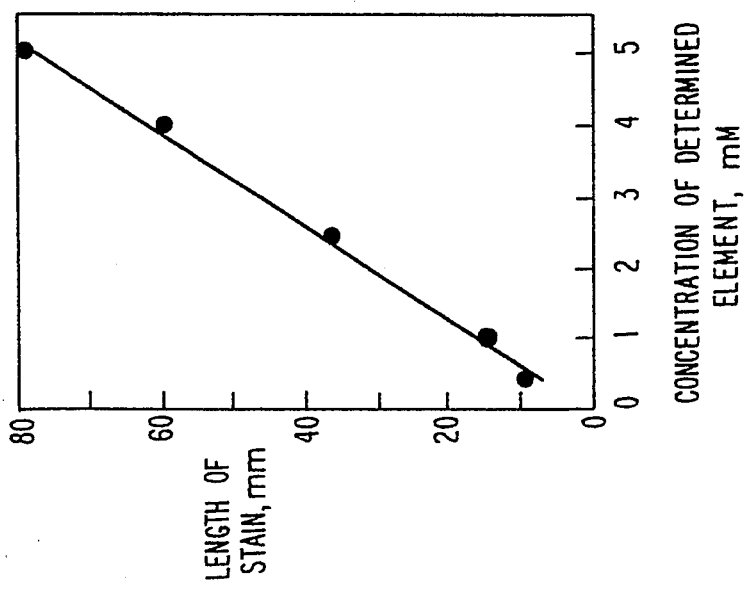
Figure 4A:
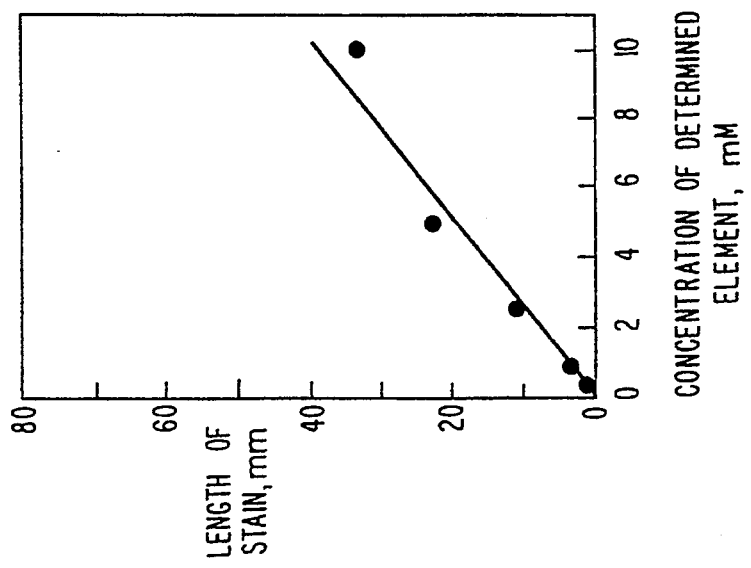

FIG. 4 depicts the response of disposable tube detectors containing glass pellets doped with 1,10-o-phenanthroline for iron(II) determination, 1-nitroso-2-naphthol for cobalt(II) and alizarin for aluminum(III) determination. The experiments depicted in FIG. 4 were carried out using glass capillaries filled with Sol-Gel pellets smaller than 0.1 mm and using capillarity force to drive the solution into the tube detectors. The color fronts (from white to red for iron, from yellow to brown for cobalt and from lilac to purple for aluminum) were sharp and could be distinguished within accuracy greater than 1 mm. An almost linear dependence of the stain length on the concentration of the analyzates is exhibited.

F. Alkalinity and Acidity Tube Detectors

In the following we demonstrate that methyl orange doped sol-gel Tube Detectors can serve as alkalinity detectors and that the length of stain produced when water is sampled through the tube detectors represent alkalinity rather than pH measurement.

Experimental

Tube Detector preparation: Tube detectors containing sol-gel glasses doped with 0.05% methyl orange were prepared according to the procedure specified in example E above. The samples containing several combinations of sodium carbonate and sodium bicarbonate solutions were pumped into the capillaries at a constant rate using a home built positive displacement pump.

Results

Table 3 depicts the length of stain produced by three sample solutions exhibiting the same pH (pH=9.7) and different alkalinities. The length of stain is almost proportional to the alkalinity (expressed in mg $CaCO_3$). Maintaining the same alkalinity (as in sample 3 and 4) and changing the pH did not change the length of stain response of the detectors.

TABLE 3

Response of Alkalinity Tube Detectors

| experiment number | Alkalinity (mg $CaCO_3$) | pH | Sampled volume (ml) | Length of Stain (mm) |
|---|---|---|---|---|
| 1 | 300 | 9.7 | 0.07 | 2.7 |
| 2 | 1,500 | 9.7 | 0.07 | 5.8 |
| 3 | 3,000 | 9.7 | 0.07 | 9.7 |
| 4 | 3,000 | 11.0 | 0.07 | 10.0 |

G. Fracture prevention

We hereby demonstrate that doping sol-gel glasses with ionic surface active agents (e.g. quarternary ammonium ions) prevents cracking of doped sol-gel glass during drying and wetting of the glasses. Glasses doped with said dopants and with photometric reagents maintain their photometric activities.

Experimental Details

Glass preparation: The experiments were carried out using Sol-Gel glasses prepared according to standard Sol-Gel procedures depicted above: In a typical procedure 5.0 ml tetramethoxysilane (Petrarch), 6.0 ml methanol and 2.4 ml water containing the reagent and cetylpyridinium bromide or cetyltrimethyammonium bromide according to the concentrations depicted below (in some cases the reagents were dissolved in the methanol) and 1 ml 0.1 mM NaOH solution (added for base catalysis) were mixed, allowed to gel for three days and then dried to constant weight at 41° C. for two weeks.

Results

Figure 5:
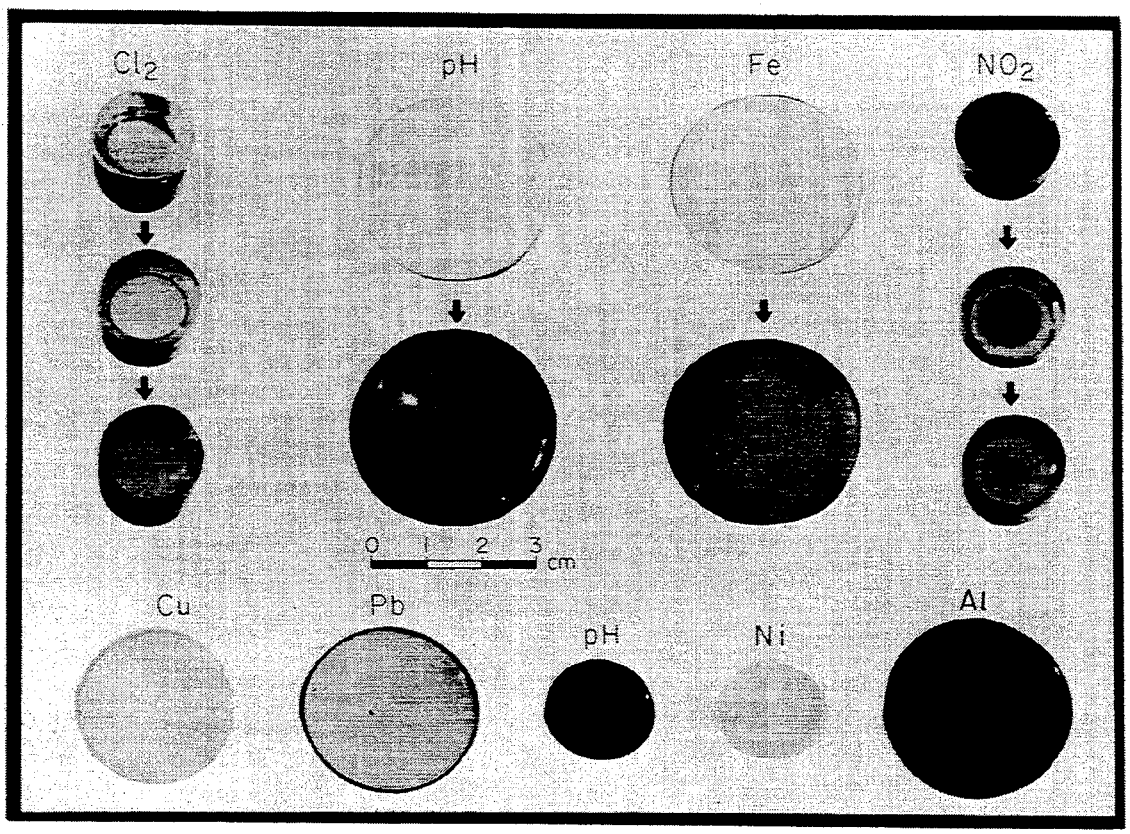
FIG. 5 discloses monolithic glass detectors doped with ionic surface active agents to prevent cracking. Upper section: detectors before and after immersion in solution containing the analyzates; lower row: monolithic glass disks.
Figure 1A:
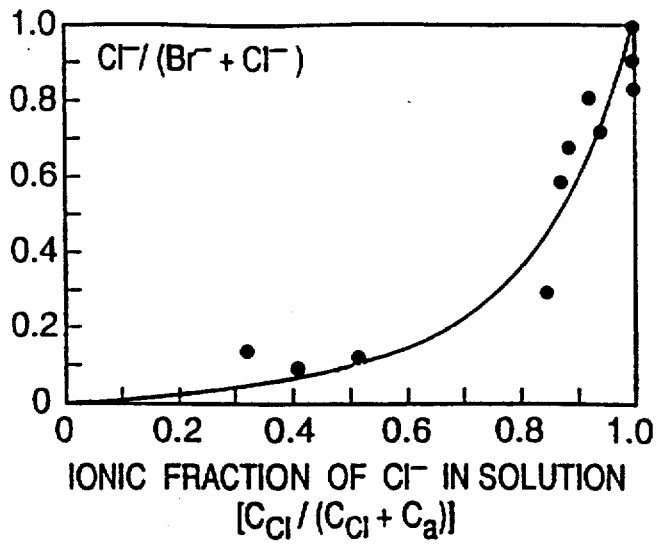
Figure 1B:
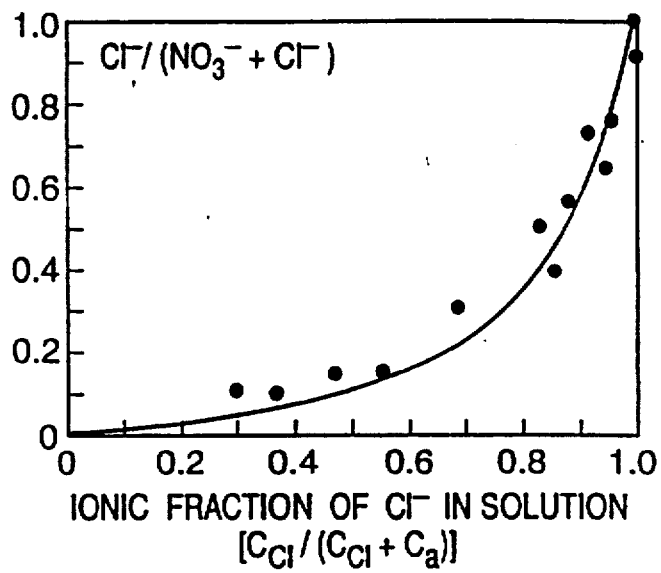
Figure 1C:
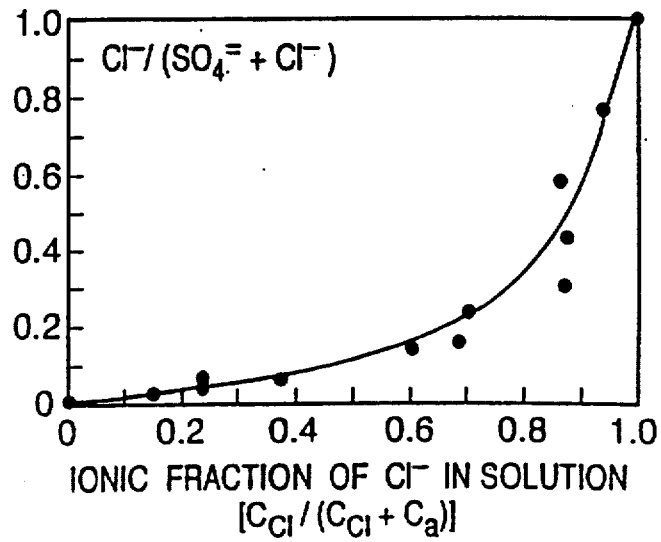

FIG. 5 depicts several typical photometric detectors containing doped surface active agents. The first upper section contains four examples of monolithic doped glasses before and after immersion in aqueous solution containing the analyzate (from left to right: Redox detector containing Diphenylaminesulfonate barium salt (1 mg) and 5 mg cetylpyridinium bromide (CPB) before and after immersion in sodium hypochlorite solution; pH indicator containing phenolphthalein (2.5 mg) and 6.6 mg cetyltrimethylammonium bromide (CTAB) before and after immersion in basic aqueous solution; iron Detector containing 1,2 mg o-phenanthroline and 5.0 mg CPB before and after immersion in a solution containing ferrous ammonium sulfate; nitrite indicator containing 4 mg 1-Naphthylenediamine dihydrochloride, 10 mg sulphanilic acid and 6 mg (CTAB). The lower row depicts few detectors (from left to right: copper detector containing 1 mg dithiooxamide and 6.25 mg CPB; lead detector containing 1 mg galocyanine and 7.5 mg CPB; pH detector containing 5 mg bromophenol and 6.6 mg CTAB; nickel detector containing 2 mg dimethyglyoxime and 6.25 mg CPB; aluminum detector containing 5 mg alizarin and 12.5 mg CPB).

In all cases the described procedure prevented cracking of the monolithic glasses even after few cycles of wetting and drying of the glasses.

We claim:

1. A process for qualitative or quantitative determination of a reactive chemical contained in a liquid sample, comprising
   (a) forming porous doped sol-gel glass pellets from a metal alkoxide by a gelling step conducted at room temperature in the presence of a colorimetric reagent dopant which produces a color change in the presence of a reactive chemical, and a drying step conducted at not greater than 41° C., the doped sol-gel glass pellets containing the colorimetric reagent dopant encapsulated therein and the encapsulated colorimetric reagent dopant being color changeable in the presence of the reactive chemical in the pores of the doped sol-gel glass pellets;
   (b) arranging the porous doped sol-gel glass pellets in a glass tube;
   (c) contacting a liquid sample containing the reactive chemical with the porous doped sol-gel glass pellets contained in the glass tube; and
   (d) measuring a length of a stained portion of the porous doped sol-gel glass pellets resulting from the colorimetric reagent dopant color change produced by reaction with the reactive chemical.

2. A process as defined by claim 1, wherein the glass tube is a capillary tube.

3. A process as defined by claim 1, wherein the liquid sample is contacted with the porous doped sol-gel glass pellets by immersing the glass tube in the liquid sample.

4. A process as defined by claim 3, wherein a capillary force drives the liquid sample through the glass tube.

5. A process as defined by claim 3, wherein a pumping means drives the liquid sample through the glass tube.

6. A process as defined by claim 1, wherein the colorimetric reagent dopant is 1,10-o-phenanthroline and the reactive chemical is iron(II) ion.

7. A process as defined by claim 1, wherein the colorimetric reagent dopant is 1-nitroso-2-naphthol and the reactive chemical is cobalt ion.

8. A process as defined by claim 1, wherein the colorimetric reagent dopant is alizarin and the reactive chemical is aluminum ion.

9. A process as defined in claim 1, wherein the colorimetric reagent dopant is an acidic pH indicator.

10. A process as defined in claim 1, wherein the colorimetric reagent dopant is an alkaline pH indicator.

* * * * *

UNITED STATES PATENT AND TRADEMARK OFFICE
CERTIFICATE OF CORRECTION

PATENT NO. : 5,371,018
DATED : December 6, 1994
INVENTOR(S) : David Avnir et al

It is certified that error appears in the above-indentified patent and that said Letters Patent is hereby corrected as shown below:

In the drawings, please replace Figures 1(a), 1(b) and 1(c) with new Figures 1(a), 1(b) and 1(c), as shown on the attached page.

UNITED STATES PATENT AND TRADEMARK OFFICE
CERTIFICATE OF CORRECTION

PATENT NO. : 5,371,018
DATED : December 6, 1994
INVENTOR(S) : David AVNIR et al.

It is certified that error appears in the above-indentified patent and that said Letters Patent is hereby corrected as shown below:

Column 1, line 53, change "aminic" to --amino--;
Column 1, line 54, change "successful" to --successfully--.
Column 2, line 21, change "$SO_4^-$" to --$SO_4^{2-}$--.
Column 5, line 19, change "$SO_4^-$" to --$SO_4^{2-}$--;
Column 5, line 28, change "$SO_4^-$" to --$SO_4^{2-}$--.
Column 6, line 3, change "ed.) in a" to --ed.). In a--.
Column 7, line 7, change "$R_sS$" to --$R_s$--.
Column 10, line 31, change "1-Naphthylenediamine" to --1-Naphthalenediamine--.

Signed and Sealed this

Sixteenth Day of May, 1995

BRUCE LEHMAN

Attest:

Attesting Officer

Commissioner of Patents and Trademarks